US 6,483,893 B1

United States Patent
Achtnig et al.

(10) Patent No.: US 6,483,893 B1
(45) Date of Patent: Nov. 19, 2002

(54) DIGITAL HIGH RESOLUTION X-RAY IMAGING

(75) Inventors: Jeffery W. Achtnig, Edmonton (CA); Terrence G. Bayrock, Sherwood Park (CA); Christopher Ciarcia, Los Alamos, NM (US); Barry A. Nonay, Edmonton (CA); Cynthia G. Pachal, St. Albert (CA)

(73) Assignee: Wuestec Medical, Inc., Mobile, AL (US)

(*) Notice: Subject to any disclaimer, the term of this patent is extended or adjusted under 35 U.S.C. 154(b) by 0 days.

(21) Appl. No.: 09/449,172

(22) Filed: Nov. 24, 1999

(Under 37 CFR 1.47)

Related U.S. Application Data (60) Provisional application No. 60/110,118, filed on Nov. 27, 1998.

(51) Int. Cl.⁷ .............................................. G01N 23/083
(52) U.S. Cl. ........................................ 378/98.12; 378/62
(58) Field of Search ............................. 378/4, 62, 98.12

(56) References Cited

U.S. PATENT DOCUMENTS

| | | | |
|---|---|---|---|
| 3,860,817 A | 1/1975 | Carmean | 250/320 |
| 4,412,346 A | 10/1983 | Takenouti et al. | 378/181 |
| 4,684,565 A | 8/1987 | Abeles et al. | 428/220 |
| 4,761,805 A | 8/1988 | Sebring | 378/181 |
| 4,821,727 A | 4/1989 | Levene et al. | 128/653 |
| 4,890,313 A | 12/1989 | Lam et al. | 378/189 |
| 4,924,487 A | 5/1990 | Nishiki | 378/190 |
| 4,979,198 A | 12/1990 | Malcolm et al. | 378/102 |
| 4,987,307 A | 1/1991 | Rizzo et al. | 250/368 |
| 4,995,068 A | 2/1991 | Chou et al. | 378/189 |
| 5,090,042 A | 2/1992 | Bejjani et al. | 378/99 |
| 5,211,165 A | 5/1993 | Dumoulin et al. | 128/653.1 |
| 5,712,890 A * | 1/1998 | Spivey et al. | 378/37 |

FOREIGN PATENT DOCUMENTS

CA    2179616    7/1994

* cited by examiner

Primary Examiner—David V. Bruce
(74) Attorney, Agent, or Firm—Fulbright & Jaworski L.L.P.

(57) ABSTRACT

A system and method for high resolution digital x-ray imaging which utilizes multiple imaging sensors is disclosed. In the preferred embodiment, the system includes multiple imaging sensors with overlapping fields of view. The imaging sensors are preferably interfaced with a general purpose computer capable of seamlessly combining the multiple images captured by the multiple imaging sensors.

21 Claims, 3 Drawing Sheets

DIGITAL HIGH RESOLUTION X-RAY IMAGING

RELATED APPLICATIONS

The present application claims the benefit of U.S. Provisional Application No. 60/110,118, filed Nov. 27, 1998, the disclosure of which is incorporated herein by reference. The present application is related to concurrently filed U.S. patent application Ser. No. 09/449,173, entitled "AUTOMATIC EXPOSURE INITIATION IN A DIGITAL CCD CAMERA X-RAY SYSTEM" (issued as U.S. Pat. No. 6,339,633), the disclosure of which is incorporated herein by reference. The present application is also related to concurrently filed U.S. patent application Ser. No. 09/449,174, entitled "OPTICAL DISTORTION CORRECTION IN DIGITAL IMAGING", the disclosure of which is incorporated herein by reference.

TECHNICAL FIELD

The present invention relates to high resolution digital imaging and in particular to a digital x-ray imaging system and method utilizing multiple digital cameras.

BACKGROUND

In conventional x-ray imaging a photographic film is exposed to visible light produced by a fluorescent imaging screen in response to x-ray energy which has passed through an object, in order to capture the image of the object being x-rayed. The x-rays are passed through the object and impinge on the fluorescent imaging screen, such as a phosphor imaging screen. The phosphor imaging screen converts some of the radiation into a selected spectral component (typically visible light). The exposure of the photographic film to the spectral component from the phosphor imaging screen produces the image of the object on the photographic film.

Recent advances in x-ray imaging however have resulted in filmless x-ray methods and apparatus. Such a system is disclosed in U.S. Pat. No. 5,309,496, entitled "FILMLESS X-RAY APPARATUS AND METHOD OF USING THE SAME", issued to Winsor, which is hereby incorporated herein by reference. In the preferred embodiment of Winsor, a video camera and a frame grabber are used to provide still x-ray images.

However, in x-ray imaging it is desirable to get very high resolution images so that a health care provider could accurately diagnose a patient. The use of photographic films as used in conventional x-ray imaging systems does not provide the high degree of resolution desirable in x-rays. Moreover, the video camera and frame grabber of Winsor do not provide the desired high degree of resolution because in the preferred embodiment video camera and frame grabber implementation of Winsor, an image in analog format is filmed by the video camera and a frame grabber used to capture one or more frames. The captured frames may then be digitized. Because of the conversion of the image from analog format to digital format, the desired degree of resolution may not be obtained. Also, as the video tube of the video camera has a fixed life span, it deteriorates over time and accordingly the quality of the image deteriorates over time, which may be evidenced for example by a decrease in the contrast of the image.

Furthermore, in any imaging system, because of the curvature of the lens (or lens assembly), more light passes through the center of the lens than through the edges. Therefore, the intensity of the pixels in the center is greater than the intensity of the pixels at the edges. Because of limitations of the video camera and frame grabber of the preferred embodiment of Winsor, the pixel contrast and/or intensities cannot be modified on an individual basis and therefore, in the final x-ray image the pixels at the center are brighter than those at the edges.

An alternative structure for capturing images is a CCD (charge coupled device) camera. However, high resolution digital CCD cameras are very expensive and still do not provide the high level of resolution necessary for diagnostic x-ray imaging. Because of the difficulty of obtaining large CCD chips of consistent quality and the cost of manufacturing such large CCD chips, multiple digital CCD cameras may be used in place of a single digital camera. The use of multiple digital cameras is known in other fields. In such applications, different cameras are used to capture different portions of the entire image thereby providing multiple images, which are later merged together in order to create a single image. However, in such applications, a known reference point is added to the original image itself. The different images are merged together using the known reference point. By utilizing the known reference point in the merging process, the combining of the images may be accomplished more efficiently. But this procedure adds unwanted artifacts (the reference point itself) to the image. The presence of artifacts in the combined image would be specially undesirable in an x-ray imaging system because of the degree of accuracy preferred in rendering a correct diagnosis of the patient based on the x-rays.

Therefore, there is a need in the art for a system and method for rendering high resolution digital x-ray images of an object.

There is also a need in the art for a system and method for quickly, accurately and seamlessly combining multiple overlapping x-ray images into a single image without adding unwanted artifacts to the final image.

SUMMARY OF THE INVENTION

These and other objects, features and technical advantages are achieved by an x-ray imaging system and method which utilizes multiple imaging sensors to acquire an image from an imaging screen.

In a preferred embodiment, the x-ray imaging system comprises at least two imaging sensors, such as digital CCD cameras, with overlapping fields of view. The digital cameras preferably acquire the image from an imaging screen, such as for example, a fluorescent phosphor screen used in x-ray imaging. The digital cameras are positioned so that the field of view of the digital cameras substantially covers the imaging screen. The use of multiple imaging sensors facilitates increasing the resolution of the image as each imaging sensor can capture a smaller portion of the imaging screen.

In the preferred embodiment, the imaging apparatus also includes a host processor based system comprising camera interfaces for receiving and processing the images from the multiple cameras. Such a host processor based system may be for example, a general purpose computer. A preferred method for combining the overlapping images is preferably implemented by software associated with such a general purpose computer. The method comprises calibrating the x-ray imaging system by combining an initial set of two or more overlapping calibration images of different sizes and orientations. During the calibration process, the amount by which an image is to be offset in order to properly align with another image is calculated. The optimal offsets for joining the images in the overlap region are preferably calculated by determining the best correlation of the images in the region common to each of the images. These optimal offsets may be stored in the computer system and used to quickly combine a subsequent series of images of substantially the same size and orientation as the calibration images.

The offsets for a particular camera setting may be calculated periodically, for example once a month, to adjust for any change in the positions of the cameras since the last calibration. Accordingly, in the preferred embodiment, the offsets need not be calculated each time the multiple images of an x-rayed object are to be joined or combined together, i.e., once the offsets for a particular camera setting using the calibration images have been calculated, the offsets may be used to quickly combine or join subsequent individual images into a single image.

Moreover, in a preferred embodiment, in order to provide seamless joining or stitching of the multiple images, the intensities of the pixels of the individual images in the overlapped region may be adjusted. Any noticeable seam between the images may be removed by gradually merging the images in the common overlapping region. This is preferably accomplished by adjusting the intensity values of the individual images in the overlap region so that there is a gradual transition from one individual image to the other.

Accordingly, it is a technical advantage of a preferred embodiment of the present invention to provide a high resolution digital x-ray imaging system.

It is another technical advantage of a preferred embodiment of the present invention to provide a seamless x-ray image.

It is still another technical advantage of a preferred embodiment of the present invention to quickly, accurately and seamlessly combine multiple overlapping images into a single image.

It is yet another technical advantage of a preferred embodiment of the present invention to combine multiple images without the use of known reference points.

It is yet another technical advantage of a preferred embodiment of the present invention to provide high resolution x-ray images without any undesirable image artifacts.

It is yet another technical advantage of a preferred embodiment of the present invention that each pixel in the overlap region can be modified individually.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION

Figure 1:
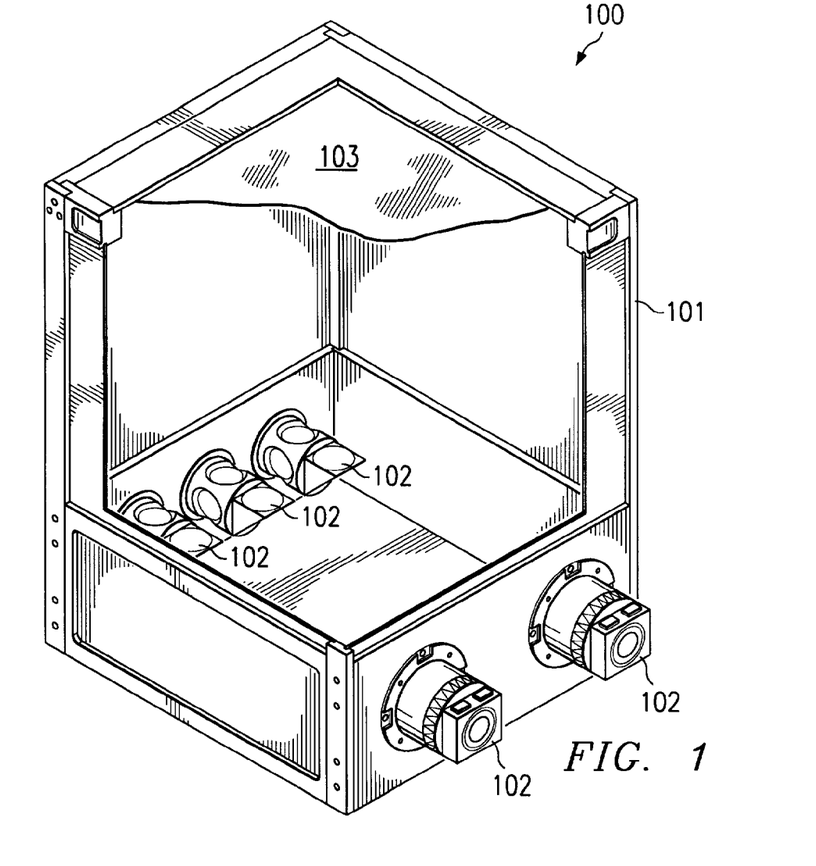
FIG. 1 shows a cutaway view of a multiple camera housing used in the present invention.

FIG. 1 shows a cutaway view of a multiple camera housing used in the imaging system of the present invention. As shown in FIG. 1, the multi-camera housing system 100 comprises a housing 101 and multiple imaging sensors 102 aligned in various orientations to capture an image from an imaging screen 103. In the preferred embodiment, the imaging system utilizes two imaging sensors. However, the present invention will be discussed. with regard to five imaging sensors in order to fully illustrate the scope of the present invention.

Housing 101 is preferably a rigid, light tight, box made of aluminum. As shown in FIG. 1, imaging screen 103 is preferably provided along the top portion of the camera housing 101. However, the housing provides a means for fixing the position of the imaging screen 103 in relation to the imaging sensors 102. The particular configuration of the housing and the cameras as shown in FIG. 1 is not relevant to the invention covered by the present application. In the preferred embodiment, the imaging sensors are digital CCD cameras and imaging screen 103 is a fluorescent phosphor screen used in X-ray imaging.

To accommodate various aspect ratios and sizes of the imaging screen 103, the number of cameras used may be varied. Thus, if desired, the number of cameras may be increased or decreased in either orientation (landscape or portrait). The housing would be resized to accommodate the different camera configurations. Moreover, as the costs of the CCD chips used in the cameras decreases higher resolution cameras can be utilized to cover more image area or to improve the digitized resolution.

Figure 2:
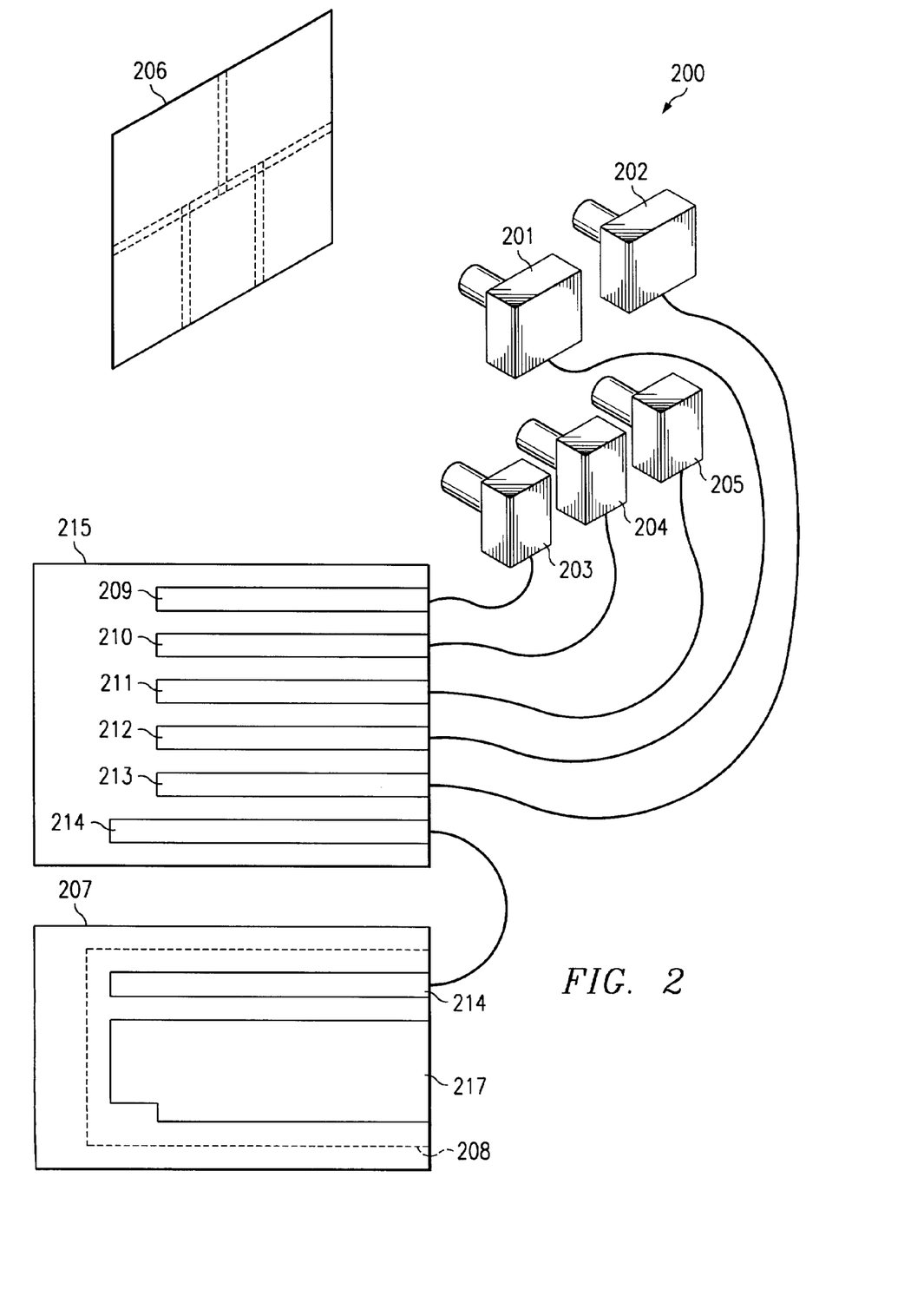
FIG. 2 is a schematic representation of an imaging system of the present invention using multiple imaging sensors.

FIG. 2 is a schematic representation of an imaging system of the present invention using the multiple imaging sensors. As shown in FIG. 2, imaging screen 206 is preferably divided into a number of overlapping portions. The overlap between the different portions of the imaging screen is denoted by the dotted lines in FIG. 2. The number of imaging sensors used in the imaging system of the present invention is preferably equal to the number of portions into which the imaging screen is divided. Each of the imaging sensors is aligned or positioned so as to capture a corresponding portion of the imaging screen 206.

Each camera is preferably connected to a host processor based system 207 by a data transfer mechanism. The host processor based system is preferably a general purpose computer, such as a Personal Computer (PC) of known and conventional configuration. Each camera is connected to a suitable camera interface card which is associated with the host system. For the five cameras shown in FIG. 2, five camera interface cards 209, 210, 211, 212, and 213 are used. The camera interface card is preferably a proprietary interface of the camera manufacturer. To accommodate multiple cameras, the host preferably supports a sufficient number of ISA (Industry Standard Architecture) bus slots on a motherboard 208 to accommodate one camera interface card per camera. If enough ISA bus slots are not available then an ISA bus expander 214 and a second ISA backplane 215 may be used for interfacing the cameras with the host processor based system. In alternative embodiments, other types of bus slots, such as PCI, and USB may be used. The host PC may also contain other devices 217 that are standard for operation of a personal computer.

Software running on the host computer facilitates interfacing with the multiple cameras shown in FIG. 2. It is important to allow the multiple cameras to operate as one large virtual camera in a timely fashion. Depending on the specific commands transmitted to the cameras, the technique of transmitting data may follow either a sequential or parallel order, i.e. data may be sent between the cameras and the host computer either in series or in parallel. The parallel method utilizes the timing pauses of the communication protocol to speed up operation by transmitting data to other cameras during a pause associated with a particular camera. When the host computer is capable of transmitting data at a higher rate than the camera interface, the parallel method may be used. Accordingly, the host computer may communicate with one or more camera(s) during protocol delays with a given camera. The host computer is capable of performing many more operations in the same amount of time as the cameras are capable. An automatic exposure initiator used to trigger the capture of images is disclosed in the above mentioned U.S. patent application, entitled "Methods and Apparatus for Automatic Exposure Initiation in a Digital CCD X-Ray System", the disclosure of which is hereby incorporated herein by reference. Another method of capturing an image would be to activate the imaging sensor as soon as the x-ray source is initiated.

Each camera of FIG. 2 is positioned so that it can capture the image in a particular portion of the imaging screen 206. For example, camera 201 is positioned to capture the image in the top left portion of screen 206, while camera 205 captures the image in the bottom right portion of the screen. Thus, the five cameras shown in FIG. 2 would capture five images, each from a different portion of the imaging screen with some overlap between adjacent images. The five images so captured are fed to the host processor based system. The host processor based system processes the images to provide a complete image. In the preferred embodiment, the different portions of the screen covered by each camera overlap in order to facilitate stitching or joining of the individual images to provide the complete image. For a given screen size and number of cameras, the resolution of the image may be increased by reducing the overlap between the different portions of the image as each camera would capture a smaller portion of the screen. However, a reduction in the overlap between the images may cause difficulties in joining or stitching the different images. In an imaging system utilizing only two cameras, the preferred amount of overlap between the individual images is 20%.

Because of the difficulty associated with positioning the cameras within the housing with respect to the imaging screen so that a desired overlap is achieved, the housing is manufactured preferably by using a CNC (computer numerically controlled) machine. However, even this method does not provide the desired positioning of the cameras with respect to the imaging screen and with respect to each other. Therefore, it is desirable to offset the individual images before joining them together in order to adjust the images to account for the difference in the actual positioning and the desired positioning of the cameras. The optimal offsets may be calculated by using calibrating images as discussed in further detail below.

Figure 3:
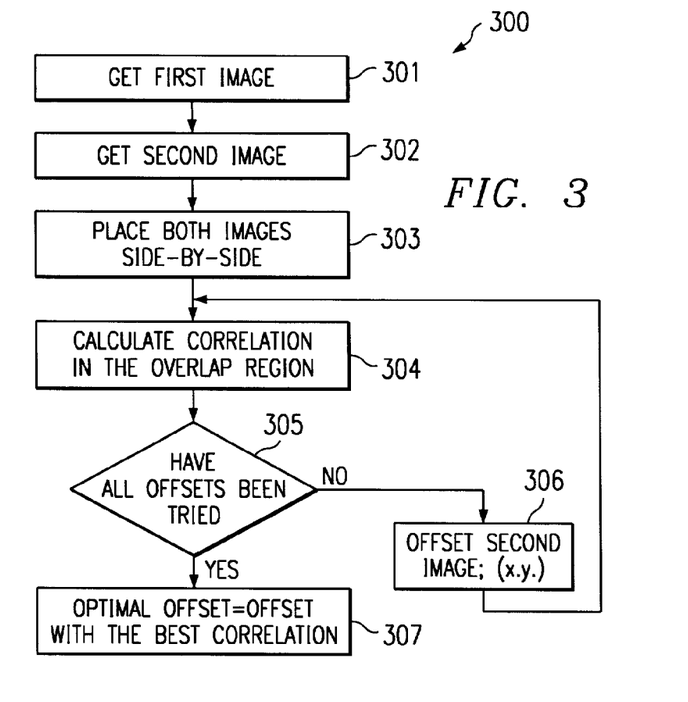
FIG. 3 is a flowchart for calculating offsets in a preferred embodiment of the present invention.

FIG. 3 shows a flowchart for calculating optimal offsets while calibrating the x-ray imaging system. In a preferred embodiment of the present invention a set of calibration images is used for this purpose. As discussed above, because of the difficulty of positioning the multiple cameras in the camera housing so that the multiple cameras preferably cover the entire imaging screen and at the same time provide a desired overlap between the portions covered by adjacent cameras, in the preferred embodiment, the imaging system is calibrated. That is, when the imaging system is initially set-up, calibrating images are used to determine the offsets by which adjacent images are adjusted in actual use of the imaging system to provide the desired stitching or combining of the individual images.

The flowchart of FIG. 3 depicts the different steps that are followed in a preferred embodiment, to compute the relative vertical and/or horizontal offsets between each of the calibration images to be combined. Suitable calibration images will be well-known to a person skilled in the art. However, a suitable calibrating image used in the preferred embodiment is a grid. Using the system as shown in FIG. 2, the image of the grid may be captured and an alignment performed, as discussed below to join the individual images into a single image. The lines of the grid may be used to match the exact position of each portion of the grid being imaged. In the preferred embodiment, a set of optimal offsets is calculated for each pair of overlapping images. As discussed below, the process of calculating optimal offsets is a highly iterative process.

As shown in FIG. 3, a first calibration image and a second calibration image are read into the host system (steps 301, 302). The two calibrating images have an overlapping region which facilitates the calculation of offsets and subsequent stitching of the images. In step 303, the first and second calibrating images are placed next to each other so that the common areas substantially overlap each other. This may be accomplished by choosing a starting point on the first calibrating image where the second calibrating image is to be placed. For example, if the two images being combined are as shown by the upper two portions of the imaging screen 206 of FIG. 2, then the second image may be placed on the first image so that the left edge of the second image corresponds substantially with the left edge of the overlapping area in the first image. If the overlap region is 100 pixels wide, then this may be accomplished easily in software, say by translating the second image to the left by 100 pixels. In step 304, the normalized correlation between all of the pixels in the area of the two images that overlap each other is calculated to determine the variance between the overlapping areas of the two images. The normalized correlation of the common image area may be calculated using a correlation equation such as:

$$\text{Normalized Correlation} = \frac{\sum_i \sum_j F(x+i, y+j) \cdot G(i, j)}{\sqrt{\left(\sum_i \sum_j F(x+i, y+j)^2\right) \cdot \sum_i \sum_j G(i, j)^2}}$$

where $F(k, l)$ is the intensity value of the $(k, l)^{th}$ pixel of the first calibrating image;

$G(k, l)$ is the intensity value of the $(k, l)^{th}$ pixel of the second calibrating image;

x is the horizontal offset;

i is the horizontal coordinate of a pixel in the common area;

y is the vertical offset; and j is the vertical coordinate of a pixel in the common area.

If desired, a subset of the common image area may be used to calculate the offsets in order to speed up the calculations with some possible loss in precision. The value of the calculated normalized correlation is preferably stored in the host computer. One of the images is then moved a little bit, say one pixel, along a particular direction and the normalized correlation value calculated again. The images are adjusted until a correlation has been calculated for all rotational, vertical and horizontal offsets within a predefined limit. As the amount of overlap between the individual images is known, this predefined limit may be set to approximately the size of the overlap region between the two calibrating images being used.

Accordingly, if the correlation for all offsets have not been calculated, then the rotational, vertical and horizontal offsets of one of the images, say the second image, is adjusted and a correlation between the new image area overlap calculated (steps 304, 305, 306). Due to the difficulty in positioning the cameras, the different sections of the imaging screen actually covered by the individual cameras may not be parallel to each other. Therefore, when combining the images, it may be desirable to rotate one of the images. The adjustment of the offsets and the calculation of correlations is repeated until a correlation has been calculated for all rotational, vertical and horizontal offsets. The offset with the best calculated correlation is deemed to be the optimal offset for combining the two images. For example, for the above equation, the offsets which give a correlation value which is closest to 1 would be the optimal offset values. Note that different correlation equations may be used depending on the particular application. The calculation of optimal offsets as described above with regard to the flowchart of FIG. 3 is repeated for all of the individual images which are adjacent to each other. These optimal offsets may be used for determining the correct location of pixels when combining individual images obtained during subsequent use of the x-ray imaging system.

Thus, once the optimal offsets for a particular setting of multiple cameras has been determined as described above, there is no need for calculating the offsets for combining subsequent images as subsequent images may be combined using the optimal offsets. However, it is desirable to calculate the optimal offsets for a particular camera setting periodically to account for any movement of the camera positions due to normal use.

Because of the differences in the CCD chips due to the manufacturing process, the image captured by different CCD chips may have different intensities. Each pixel in a CCD image may be normalized by using dark frame and flat field images. Dark frame images are acquired in total darkness; the intensity values obtained indicate noise due to heat and electronics. Flat field images are acquired in an integrating sphere in which the light is substantially uniform. Differences between pixels in a flat field image indicate differences in operating characteristics of cells within the CCD chip. Each pixel within a digital image is corrected on a pixel-by-pixel basis using the following formula:

$$I_{improved} = (I_{original} - I_{dark})/(I_{flat} - I_{dark}), \text{ where:}$$

$I_{improved}$ is the improved image;

$I_{original}$ is the original image;

$I_{flat}$ is the flat field (image with substantially the same amount of light on each pixel); and $I_{dark}$ is the dark frame (image with no light).

Thus, the variations between the images may be removed by the above process. After dark frame and flat fielding, each pixel has a normalized value between 0 and 1, wherein the brightest pixels have a value of 1. The pixels are then scaled by a scaling factor. For example, when using 8 bit pixels, the normalized pixel values are scaled by $2^8$. Thus, the individual images from the different cameras are equalized using dark framing and flat fielding.

After normalization and scaling, the remaining differences in the intensities of the pixels is due to the differences in the refractive properties of the optical lens used in the different cameras. These remaining differences are removed by the merging process described below with regard to step 406 of FIG. 4.

Figure 4:
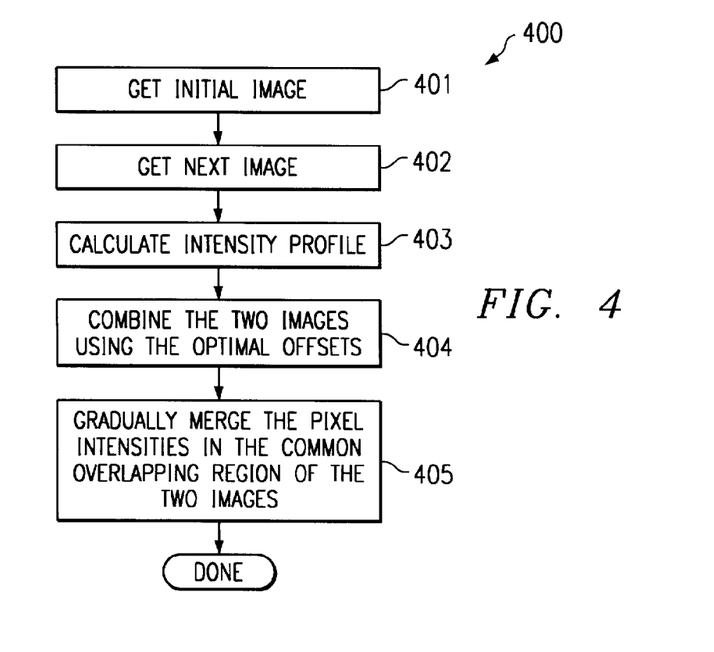
FIG. 4 is a flowchart for joining multiple images in a preferred embodiment of the present invention.

FIG. 4 shows a flowchart for joining multiple x-ray images in a preferred embodiment of the present invention. The optimal offsets calculated by the preferred embodiment method of FIG. 3 discussed above, is used to combine or stitch the x-ray images of substantially the same size and orientation as the calibration images.

As shown in FIG. 4, a first x-ray image is read into the host system (step 401). A second x-ray image to be stitched with the first x-ray image and having an overlapping region common with the first x-ray image is also read into the host system (step 402). In step 403, the intensity profiles of the pixels in the overlap region of the two images are separately calculated. One simplified approach to doing this would be to calculate the average pixel intensity value in each image's common overlapping region. In the preferred embodiment, this is accomplished by adding the intensity values of all the pixels in the overlap region of the first image and dividing it by the number of pixels in the overlap region. The intensity profile of the pixels in the common region of the second image is similarly calculated by adding the intensity values of all the pixels in the overlap region of the second image and dividing it by the number of pixels in the overlap region.

In step 404, the two images are combined together. Since the optimal offset values have already been obtained by the calibrating process discussed above, the positions of the two images to be combined with respect to each other is also known. The two images may be combined for example, by taking the first image and aligning the second image on top of the first image using the known optimal offset values. However, the combined image thus obtained may have a visible seam in the area of the overlap giving the impression that the two individual images have been stitched together.

Accordingly, in step 405, any noticeable overlap or seam between the images may be removed by gradually merging the pixel intensities of the two images within the overlap region. In the merging process, the pixel intensity values of the combined image in the overlap region is changed to provide a combined image having a smooth transition from one portion of the image to the other. In the preferred embodiment, the merging process starts in the center of the overlap region and extends outwards, i.e. the intensities of the pixels in the center of the overlap region are changed first.

The images are gradually merged together over the entire overlapping region (or a portion thereof) to remove any indication of a seam between the images. The difference in the intensity profiles of the pixels in the common region of the individual images as calculated above is preferably used to provide the smooth transition from one image to the other.

Figure 5:
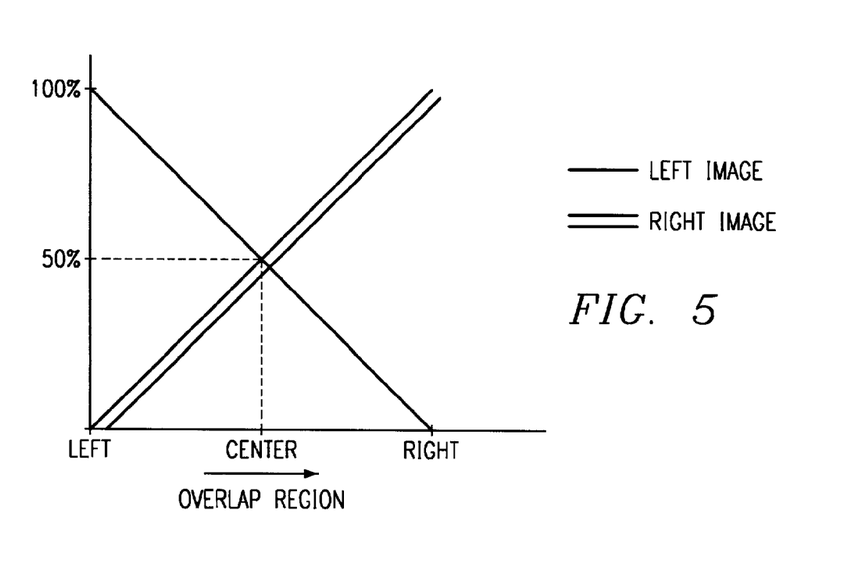
FIG. 5 shows a diagram for pixel intensity value contributions from two images.

In the preferred embodiment, the pixel intensity value at the center of the overlap region is the average of the intensity profile values as calculated above for the two images. Thus, 50% of the new pixel intensity value is obtained from one image and the other 50% is obtained from the second image. The pixel intensity values are gradually changed towards the outer edge of the common overlap region, such that at either edge of the overlapping region, 100% of the new pixel value is obtained from the image on the corresponding side of the overlapping region. For example, assume that the intensity profile value calculated above for the common region of the first image (say, the left image) is 100 and that the intensity profile value for the common region of the second image (say, the right image) is 80. If the overlap region is 100 pixels wide, then the pixel intensities in the center of the overlap region (say at the 50th pixel), would be ((100*½)+(80*½)=)90. Moving left from the center of the overlap region, the pixel intensities would be increased gradually so that the intensity of the pixels along the left edge of the overlap region would be (100*1+80*0=)100. Moving right from the center of the overlap region, the pixel intensities would be decreased gradually so that the intensity of the pixels along the right edge of the overlap region would be (100*0+80*1=)80. This is illustrated in the diagram of FIG. 5, which shows that at the left most point of the overlap region, 100% of the pixel intensity value depends on the intensity profile value of the left image. The pixel intensity values at the center of the overlap region depend 50% on the intensity profile of the left image and 50% on the intensity profile of the right image. Because of the gradual change in the intensity values of the pixels in the common area from one image to the other, the combined image does not have any noticeable seam. The steps for combining the individual images as described above with regard to the flowchart of FIG. 4 are repeated until all the individual images have been combined to form the entire image. The final result is a seamlessly combined image.

Although the steps of combining the images and merging the pixel intensities has been described above as two separate steps, the invention is not so limited and in alternate embodiments the two steps 404 and 405 of the flowchart of FIG. 4 may be combined.

Although the present invention has been described above, with regard to changing the intensities of the pixels from the center of the overlap region towards the edge, the invention is not so limited and in alternative embodiments, the pixel intensities may be changed from the edge towards the center, if desired. Moreover, any known normalized correlation equation may be used to calculate the optimal offset values. Furthermore, there is no limitation on the number of sections a particular imaging screen may be divided into for capturing individual images.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method for removing a seam from a digital x-ray image comprising of a first x-ray image and a second x-ray image wherein said first x-ray image and said second x-ray image have a common overlapping area, said method comprising the steps of:

calculating a first intensity profile value for the pixels in said overlap area of said first x-ray image;

calculating a second intensity profile value for the pixels in said overlap area of said second x-ray image; and adjusting intensity values of pixels of said digital x-ray image in said common overlap area, wherein said adjustment of values of pixels depends in part on said calculated first and second intensity profile values and wherein said adjustment of intensity values substantially removes a seam from said digital x-ray image.

2. The method of claim 1, wherein the intensity value of the $i^{th}$ pixel ($I_i$) along a particular axis of said digital x-ray image in said common overlap area is given by the equation:

$$I_i = P1*((\text{width}-i)/\text{width}) + P2*(i/\text{width}),$$

wherein width is the width of said common overlap area along said axis;

P1 is said first intensity profile value;

P2 is said second intensity profile value; and i varies from 0 to width.

3. The method of claim 1, wherein said calculating said first intensity profile value step comprises the substeps of:

summing the intensity values of all pixels in said common overlap area of said first x-ray image to provide a first summed intensity value; and dividing said first summed intensity value with the number of pixels in said common overlap area of said first x-ray image to provide said first intensity profile value.

4. The method of claim 1, wherein said calculating said second intensity profile value step comprises the substeps of:

summing the intensity values of selected pixels in said common overlap area of said second x-ray image to provide a second summed intensity value; and dividing said second summed intensity value with the number of said selected pixels used to calculate said second summed intensity value.

5. The method of claim 1, wherein the intensity of a pixel in said overlap area depends on its distance from the non-overlapping portion of said first x-ray image.

6. The method of claim 5, wherein the intensity of said pixel depends on its distance from the non-overlapping portion of said second x-ray image.

7. The method of claim 1, wherein said first x-ray image and said second x-ray image have been captured by different imaging sensors with overlapping fields of view.

8. A method for providing a seamless x-ray image in a high resolution digital x-ray imaging system, said method comprising the steps of:

determining optimal offsets for aligning a first x-ray image and a second x-ray image with respect to each other, wherein said first and second x-ray images have a common overlapping area, wherein said determining step comprises the substeps of:

a. placing said second x-ray image on top of said first x-ray image such that said first and second x-ray images overlap each other;
b. calculating a normalized correlation value for all pixels in at least a portion of said overlap area;
c. storing said calculated normalized correlation value;
d. moving said second x-ray image by a predefined number of pixels along a selected direction; and
e. iteratively repeating above steps b-d a predefined number of times stitching said first and second x-ray images in part utilizing said optimal offsets to provide a first combined x-ray image; and providing a substantially seamless x-ray image from said first combined x-ray image.

9. The method of claim 8, flier comprising the step of:
interfacing said first digital camera and said second digital camera with a processor based system to provide said first x-ray image and said second x-ray image to said processor based system.

10. The method of claim 8, wherein said determining step further comprises the substep of:
selecting a desired normalized correlation value from said stored normalized correlation values.

11. The method of claim 10, wherein the position of said second x-ray image with respect to said first x-ray image that provides said desired normalized correlation value gives the value of said optimal offsets.

12. The method of claim 8, wherein said stitching step comprises the substep of:
aligning said second image on top of said first image utilizing said determined optimal offsets to provide said first combined x-ray image.

13. The method of claim 8, wherein said providing step comprises the substep of:
calculating an intensity profile for the pixels in said overlap area of said first x-ray image.

14. The method of claim 13, wherein said providing step further comprises the substep of:
calculating an intensity profile for the pixels in said overlap area of said second x-ray image.

15. The method of claim 14, wherein said providing step further comprises the substep of:
changing the intensities of pixels in said overlap area of said first combined x-ray image to provide a gradual transition from said first x-ray image to said second x-ray image.

16. The method of claim 15, wherein the intensity of a pixel in said overlap area depends on its distance from the remaining portion of said first x-ray image.

17. The method of claim 15, wherein the intensity of a pixel in said overlap area depends on its distance from the remaining portion of said second x-ray image.

18. The method of claim 15, wherein the intensity of a pixel in said overlap area depends on said intensity profiles of said first x-ray image and said second x-ray image.

19. The method of claim 8, further comprising the step of:
positioning a first digital camera in front of an imaging screen to provide said first x-ray image prior to said determining step; and
positioning a second digital camera in front of said imaging screen to provide said second x-ray image prior to said determining step.

20. A method for combining x-ray images, said method comprising:
providing a first x-ray image and a second x-ray image, wherein said first and second x-ray images have a common overlapping area;
stitching said first and second x-ray images to provide a first combined x-ray image; and
providing a substantially seamless x-ray image from said first combined x-ray image, wherein said providing step comprises the substeps of:
determining a first intensity profile value for the pixels in said overlap area of said first x-ray image;
determining a second intensity profile value for the pixels in said overlap area of said second x-ray image; and
modifying intensity values of pixels of said first combined x-ray image in said common overlap area, wherein said adjustment of values of pixels depends in part on said calculated first and second intensity profile values and wherein said adjustment of intensity values substantially removes a seam from said first combined digital x-ray image.

21. The method of claim 20 wherein the intensity value of the $i^{th}$ pixel ($I_i$) along a particular axis of said digital x-ray image in said common overlap area is given by the equation:

$$I_i = P1*((\text{width}-i)/\text{width}) + P2*(i/\text{width}),$$

wherein
width is the width of said common overlap area along said axis;
P1 is said first intensity profile value;
P2 is said second intensity profile value; and
i varies from 0 to width.

* * * * *

UNITED STATES PATENT AND TRADEMARK OFFICE
CERTIFICATE OF CORRECTION

PATENT NO. : 6,483,893 B1 Page 1 of 1
DATED : November 19, 2002
INVENTOR(S) : Jeffery W. Achtnig et al.

It is certified that error appears in the above-identified patent and that said Letters Patent is hereby corrected as shown below:

Column 11,
Line 15, "flier" should be -- further --.

Signed and Sealed this

Fourth Day of March, 2003

JAMES E. ROGAN
*Director of the United States Patent and Trademark Office*